(12) United States Patent
Woehrle

(10) Patent No.: US 9,220,421 B2
(45) Date of Patent: Dec. 29, 2015

(54) NON-INVASIVE BLOOD PRESSURE MONITORING SYSTEMS

(75) Inventor: Dieter Woehrle, Waiblingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 295 days.

(21) Appl. No.: 13/377,826

(22) PCT Filed: Jun. 14, 2010

(86) PCT No.: PCT/IB2010/052632
§ 371 (c)(1),
(2), (4) Date: Dec. 13, 2011

(87) PCT Pub. No.: WO2010/150128
PCT Pub. Date: Dec. 29, 2010

(65) Prior Publication Data
US 2012/0089034 A1    Apr. 12, 2012

(30) Foreign Application Priority Data
Jun. 22, 2009    (EP) ..................................... 09163330

(51) Int. Cl.
*A61B 5/022* (2006.01)
*A61B 19/00* (2006.01)
*A61B 5/00* (2006.01)

(52) U.S. Cl.
CPC .............. *A61B 5/022* (2013.01); *A61B 19/44* (2013.01); *A61B 5/7495* (2013.01); *A61B 2560/0456* (2013.01); *A61B 2562/08* (2013.01)

(58) Field of Classification Search
CPC ........................ A61B 5/022–5/02255; A61B 2019/44–2019/448; A61B 2562/08

USPC ................................................... 600/490–499
See application file for complete search history.

(56) References Cited

U.S. PATENT DOCUMENTS

| | | | |
|---|---|---|---|
| 4,216,779 A | 8/1980 | Squires et al. | |
| 4,501,280 A | 2/1985 | Hood, Jr. | |
| 5,179,957 A * | 1/1993 | Williams | 600/499 |
| 6,068,601 A | 5/2000 | Miyazaki et al. | |
| 6,344,025 B1 * | 2/2002 | Inagaki et al. | 600/490 |
| 6,351,658 B1 | 2/2002 | Middleman et al. | |
| 6,450,966 B1 | 9/2002 | Hanna | |
| 6,676,600 B1 * | 1/2004 | Conero et al. | 600/438 |
| 6,884,255 B1 * | 4/2005 | Newton | 606/202 |
| 7,204,425 B2 * | 4/2007 | Mosher et al. | 235/492 |
| 7,204,808 B1 * | 4/2007 | Friedman et al. | 600/490 |
| 7,398,803 B2 * | 7/2008 | Newton | 141/95 |
| 2003/0093001 A1 * | 5/2003 | Martikainen | 600/499 |
| 2003/0135124 A1 | 7/2003 | Russell | |
| 2004/0127937 A1 * | 7/2004 | Newton | 606/202 |
| 2006/0293600 A1 * | 12/2006 | Wawro et al. | 600/490 |
| 2007/0088224 A1 * | 4/2007 | Friedman et al. | 600/490 |
| 2007/0129636 A1 * | 6/2007 | Friedman et al. | 600/481 |

(Continued)

FOREIGN PATENT DOCUMENTS

EP    1818012 A1    8/2007
JP    H0425009 B2    4/1992

*Primary Examiner* — Navin Natnithithadha
*Assistant Examiner* — Meredith Weare

(57) ABSTRACT

The present invention relates to the field of non-invasive blood pressure (NIBP) monitoring systems and particularly to a system that allows the identification of other components of the system via coding elements that are readable without the need for placement of this system components to the body of a patient.

19 Claims, 3 Drawing Sheets

(56) References Cited

U.S. PATENT DOCUMENTS

| | | |
|---|---|---|
| 2007/0265877 A1 | 11/2007 | Rice et al. |
| 2007/0282175 A1* | 12/2007 | Urbaszek et al. ............ 600/300 |
| 2008/0243010 A1* | 10/2008 | Kulik ............................ 600/499 |
| 2009/0156946 A1 | 6/2009 | Lane et al. |
| 2009/0171222 A1 | 7/2009 | Valdes |

* cited by examiner

NON-INVASIVE BLOOD PRESSURE MONITORING SYSTEMS

FIELD OF THE INVENTION

The present invention relates to the field of non-invasive blood pressure (NIBP) monitoring systems and particularly to a system that allows the identification of other components of the system via coding elements that are readable without the need for placement of this system components to the body of a patient.

BACKGROUND OF THE INVENTION

Blood pressure (BP) is the pressure (force per unit area) exerted by circulating blood on the walls of blood vessels. Usually it refers to brachial arterial pressure, i.e. the pressure in the major arteries of the upper left or right arm. For each heartbeat, blood pressure varies between systolic and diastolic pressures. Systolic pressure is peak pressure in the arteries, which occurs near the end of the cardiac cycle when the ventricles are contracting. Diastolic pressure is minimum pressure in the arteries, which occurs near the beginning of the cardiac cycle when the ventricles are filled with blood. The BP constitutes one of the principal vital signs and thus needs to be determined often, quickly and accurately.

For this reason automated non-invasive blood pressure (NIBP) monitoring has become standard in most clinical settings. It is increasingly used as an alternative to invasive blood pressure as it is simpler, quicker, requires less expertise in fitting, is less unpleasant for the patient and has virtually no complications.

Most NIBP monitors employ either the auscultatory or oscillometric method to non-invasively estimate the arterial blood pressure.

In the auscultatory method an inflatable cuff is placed at the upper arm and a microphone e.g. a stethoscope is placed over the brachial artery distal to the cuff e.g. at the elbow. Then the cuff is inflated to above systolic pressure. During the subsequent slow pressure release (2 mmHg/s) a repetitive clear tapping sound appears (so-called Korotkoff sounds) when the blood starts to flow in the artery. It corresponds to the systolic pressure. The cuff pressure is further released until no sound can be heard (fifth Korotkoff sound). The pressure at that point corresponds to diastolic blood pressure.

The most prevalent class of noninvasive blood pressure monitors utilize the oscillometric method, and features an inflatable cuff which is fitted over a limb of the patient, for example at the brachial artery. Through a complex system of inflation and/or deflation steps, the monitor senses small changes in cuff pressure resulting from the pulsating arteries under the cuff, the so-called oscillations, and determines mean arterial pressure, systolic pressure, diastolic pressure, and heart rate from the oscillations seen at different cuff pressures.

In both techniques the properties and size of the different system components e.g. the cuff are critical to the measurement quality and accuracy.

In order to facilitating correct sizing and usage of blood pressure cuffs during NIBP measurements the US 2008243010 discloses a cuff having an identifier and an aperture. After the cuff has been applied to a patient the identifier can only be read through the aperture, if the cuff is applied correctly i.e. in a desired configuration to a patient. Moreover the US 2008243010 discloses that a processor which is in operative communications with the cuff is configured to initiate a blood pressure measurement only when then identifier can be read through the aperture.

A disadvantage of such a system is that it only determines whether the cuff suits a particular patient but not whether other components of the system e.g. the hose suit the patient or match the chosen cuff.

A further disadvantage of such a system is that the identifier can only be read, if a cuff of appropriate size is used and the cuff is wrapped around the patient's limb correctly. Reading of the identifier may occur prior to the application of the cuff to the patient, but then the explicit intention of the US 2008243010, namely to ensure the correct cuff size, cannot be achieved.

Another disadvantage of such a system is that the measurement can be started remotely but the device carrying out the measurement has to be connected via a comparatively long hose to the cuff. Thus kinking of the hose might occur on the way from the device to the cuff, which could distort the measurement and lead to incorrect results which in turn could lead to an incorrect diagnosis and thereby harm the patient.

SUMMARY OF THE INVENTION

Thus it is an object of the present invention to prevent one or more of the above mentioned disadvantages and therefore provide a system for non-invasive blood pressure (NIBP) measurement which allows simple and quick identification of one or more system component(s).

In particular it is an object of the present invention to provide a system that identifies its component(s) independently from the suitability for the patient, correct application and/or validity of the chosen combination of system components.

It is another object of the present invention to provide a method for the identification of one or more system components of a non-invasive blood pressure system without the need for correct placement of the system components to the body of a patient.

In particular it is an object of the present invention to provide a method for ensuring an exact correlation and storage of the outcome from the blood pressure measurement to the patient and, respectively, the patient record.

These objects are achieved by the non invasive blood pressure measuring system and the method for the identification of one or more system components of a non-invasive blood pressure system as set forth in the independent claims. The dependent claims indicate preferred embodiments. In this context it is noteworthy to mention that all ranges given in the following are to be understood as that they include the values defining these ranges.

The invention is directed at a non-invasive blood pressure measuring system comprising a monitor and one or more further system components, wherein the monitor has a reading unit for the wireless identification of at least one of the one or more further system components, having a coding element that is readable without the need for placement of the system components to the body of a patient.

Such a system unambiguously identifies one or more of its components and thus facilitates the assembly and usage of appropriate components that match each other as well as the individual patient. Moreover this system achieves a greater accuracy e.g. if monitor knows properties of the applied cuff, then the mean arterial pressure, systolic pressure, and diastolic pressure calculation can be adjusted accordingly.

Preferably such a system correlates and stores the outcome of the blood pressure measurement automatically with the patient data. In order to do so, the system links the information encoded by the coding element with the outcome of the blood pressure measurement and the specific patient data.

A person skilled in the art has a good understanding of the parts a non-invasive blood pressure measuring system entails, for example a measuring device, an analysis unit, a pump, a valve, an inflatable cuff at least one hose etc.

As used herein the term "monitor" refers to a system component of the blood pressure measuring system comprising at least a reading unit, a measuring device, that carries out the blood pressure measurement, an analysis unit, that stores, analyses and displays the outcome of he blood pressure measurement, and a deflating/inflating mechanism. The monitor is placeable at any suitable location as long as the transmission of the data is ensured.

As used herein the term "coding element" refers to a data storage that saves information and from which this information is readable again. It is possible to use either a coding element, which itself transmits the stored information autonomously to a reader, or a passive coding element, which requires a reader to provoke signal transmission. The coding element can be attached to or mounted inside a system component. Alternatively, the coding element can be attached to or mounted inside any element that stays together with the system components for at least a period of time, e.g. the time the patient requires blood pressure monitoring.

In a preferred embodiment the coding element is writeable, which means the coding elements is inscribable once or rewritable, i.e. onto which information can be written several times and from which information can deleted or replaced by new information.

Preferably the coding element
a) has a unique feature e.g. a unique number as it is the case for RFID tags, which is allocated to a specific patient and thus usable to identify and track this patient, or
b) is writable with a specific information, for instance a patient identifier or operational characteristics of a system component
c) has a unique feature as in a) or is writable as in b) and sends this encoded information to the monitor and/or a patient record i.e. a central database.

In all of these cases the encoded information is always readable by a reading unit.

Examples for coding elements are RFID tags, memories, bar codes, color codes, resistors, capacitors, inductors or any other electronic components. Examples for memories as coding elements are volatile or non-volatile electronic storage systems such as DRAM, SRAM, PROM, EPROM, EEPROM or flash memory. In a different preferred example the coding element is a bar code that is readable by an optical scanner.

As used herein the term "patient record" refers to the medical data of the patient, that is stored e.g. as electronic patient file. The patient record includes at least the number allocated to the patient upon registration, e.g. upon admittance to the hospital or practice.

As used herein the term "electronic circuit" refers to a closed path formed by the interconnection of electronic components through which an electric current can flow.

As used herein the term "reading unit" or "reader" refers to a device that can read the information stored on the coding element and can optionally write information to the coding element, for instance a RFID reader. The reader may include an antenna.

The term "identification" refers to the process of reading out information and interpreting this information in order to recognize a person or an object, or link different information. The term "wireless identification" refers to an identification process that functions without any connection by electrical cables between the reading unit and the coding element.

As used herein the term "information" refers to facts encoded by the coding element such as physical and/or operational characteristics about the components or patient specific data. Physical facts about the components are for example characteristics of the hose such as length, dead space, manufacturer, production date code and/or other properties (pneumatic resistance, damping, etc.) or characteristics of the cuff such as cuff size (pediatric, adult, large adult, etc. and/or bladder width and length and/or intended limb circumference range), cuff type (reusable, single patient, etc.), patient category (neonate, pediatric, adult), manufacturer, production date code or other properties (elasticity, volume, material, etc.). Examples for patient specific data are the patients name or number, but also the required cuff size, the results of the last blood pressure measurement and other facts. Moreover if a readable and writeable coding element is used, the stored information can be a patient ID and/or patient demographics, which then can be used to identify the patient, if another monitor is connected to the patient. This leads to a considerably improved patient tracking.

During the use of the system for blood pressure measurement the information for example indicates that the parameters of the different components fit to each other, e.g. the cuff size and the hose length and/or width suit each other and the limb size of a patient, e.g. according to the specifications provided by the cuff manufacturer, to ensure correct blood pressure readings and optimal patient safety. This is especially important since completely different cuff and hence hose sizes are necessary for people of different sizes, i.e. an infant, a child, a regular adult, a medium-sized adult or a large adult.

As used herein the term "patient identifier" refers to any information that can unambiguously specify a particular patient, for instance a unique number, a patient ID, a patient's name, a symbol or an abbreviation.

In a preferred embodiment the non-invasive blood pressure system comprises besides the monitor at least one further component selected from the group consisting of a cuff, a rack, an analysis unit, a measuring device, a reading unit, a electronic pressure transducer (pressure sensor), a connecting hose, an extension hose, a microphone, a battery pack, a display and a deflating/inflating mechanism (air pump).

If a system component is provided with a coding element, this system component preferably can be exchanged by the user.

The hose used in the blood pressure measuring system connects the cuff with the measuring device. In one embodiment the hose is (dis)connectable from the cuff but permanently attached to the monitor. In another embodiment the hose is (dis)connectable from the monitor but permanently attached to the cuff. In a further embodiment the hose is disconnectable from both the cuff and the monitor. In yet another embodiment more than one hose is used in the blood pressure measuring system.

The rack used in the blood pressure measuring system supports other system components, in particular the rack is designed to hold the monitor. In a preferred embodiment the connection between the rack and the cuff is reversible, thus the rack can be connected and disconnected from the cuff, which means it is not permanently attached to the cuff.

In a preferred embodiment of the invention the hose comprises a coding element encoding information for ensuring the correct use of the components of the system and matching of the system to the individual patient during blood pressure measurements. Preferably the hose is the only connection between the cuff and the monitor. In use, the hose connects the cuff to the monitor and hence to the inflating-deflating mechanisms associated with the monitor. The coding element comprised in the hose encodes information about the hose and/or the patient for determining physical and/or operational characteristics of the hose and/or physical or other information about the patient. In a basic variant the coding element encodes at least the size of the hose.

In another preferred embodiment different cuffs are connectable to various hoses. For example if the monitor is located separate from the other system components it might be necessary to use hoses of different lengths for different patients depending for instance on where in a room blood pressure readings can be conveniently taken from a patient e.g. maybe the patient is sitting or lying down. In such a circumstance it is important that the system unambiguously identifies the cuff and the hose that are to be used to be able to determine whether the two match. If for example a hose is used which is too long and has to low inner diameter, i.e. too large flow resistance, this could lead to less than optimal inflation and deflation of the cuff and possibly a wrong diagnosis based on the reading and hence results in harm for the patient. Thus, in a further preferred embodiment both the cuff and the hose comprise a coding element encoding also information about physical and/or operational characteristics of the respective cuff and hose so that the system can unambiguously identify the cuff and the hose in order to determine whether the two match.

In another preferred embodiment the hose is permanently attached to the cuff but can be detached and attached to the monitor or the deflating/inflating mechanism. Preferably this hose is provided with a coding element that encodes the information associated with the cuff. Preferably, the coding element specifies at least the size of the cuff. In another variant of this embodiment the hose comprises a coding element that encodes the information associated with the patient. Preferably, the coding element encodes at least the patients name and/or a number that identifies the patient for instance in a central database.

In yet another preferred embodiment both the hose and the rack associated with the cuff and/or the cuff itself are provided with a coding element. In one embodiment of such an arrangement the coding elements encode at least information of the cuff and the hose respectively. The monitor preferably checks the compatibility of the cuff parameters and the hose parameters before the measurement of the blood pressure is initiated. If the monitor detects that the cuff and hose are incompatible it prevents the start of the measurement and gives a hint to the operator including instructions for the right system components that have to be used. In another variant of such an arrangement also patient specific information is provided on one or more of the coding elements so that the system can compare the newly obtained (read) information with pre-determined data for a specific patient. Thus the correctly assembled blood pressure system can be arranged before the cuff (or any other component of the system) is applied to the patient.

In a further preferred embodiment the coding element encodes information that is readable by electromagnetic radiation. Electromagnetic radiation is classified into several types according to the frequency of its wave; these types include (in order of increasing frequency and decreasing wavelength): radio waves, microwaves, terahertz radiation, infrared radiation, visible light, ultraviolet radiation, X-rays and gamma rays.

The electromagnetic radiation i.e. the waves can be used to carry information by varying a combination of amplitude, frequency and/or phase of the wave within a frequency band. A person skilled in the art has no problem choosing the correct type of reader for a given coding element to access the information encoded by the coding element.

In a preferred embodiment the coding element encodes information that is readable by high frequency transmission or infrared transmission.

High frequency refers to wavelengths with a frequency of 3 MHz to 5.75 GHz. In a preferred embodiment the frequency is 13.56 MHz. In a further preferred embodiment the frequency ranges from 2.4 GHz to 5.725 GHz, thus including technologies such as, WLAN and WPANs etc. A wireless local area network (WLAN) is a network whose interconnections between nodes is implemented without the use of wires. The network typically links two or more devices using spread-spectrum or OFDM modulation technology to enable communication between devices in a limited area. This gives users the mobility to move around within a broad coverage area and still be connected to the network.

Infrared transmission or infrared (IR) radiation is electromagnetic radiation, whose wavelength spans roughly three orders of magnitude (750 nm and 100 μm). IR data transmission is for example employed in short-range communication among computer peripherals and personal digital assistants. These devices usually conform to standards published by IrDA, the Infrared Data Association. Infrared communications are useful for indoor use in areas of high population density. IR does not penetrate walls and so does not interfere with other devices in adjoining rooms.

In a further preferred embodiment the coding element is a barcode. A barcode is an optical machine-readable representation of data. Originally, bar codes represented data in the widths (lines) and the spacings of parallel lines, and may be referred to as linear or 1D (1 dimensional) barcodes or symbologies. By now also 2 dimensional (2D) matrix codes or symbologies using patterns of squares, dots, hexagons and other geometric patterns within images are employed. Although 2D systems use symbols other than bars, they are generally referred to as barcodes as well.

In an especially preferred embodiment the coding element is a radio-frequency identification (RFID) tag. There are generally two types of RFID tags: active RFID tags, which contain a battery and can transmit signals autonomously, and passive RFID tags, which have no battery and require an external source to provoke signal transmission. RFID tags are preferred as coding element, because the tags can be read by the monitor over a distance from several centimeters to several meters (depending on antennas and output power of the RFID reader) without the need for an electrical connection between the monitor and other system components, e.g. the cuff.

In a preferred embodiment of the invention a rack is attached to the cuff. The rack is used to hold other necessary system components of the blood pressure measuring system, in particular the monitor. This arrangement has several advantages. For one the patient is not tethered to a separate monitor by the hose and can freely move around. Further the operator does not have to leave the patient to see the outcome of the measurement at a separate monitor and also problems accessing any part of the NIBP system are reduced to a minimum. Moreover also the other components of the system are very small and require less room both during storage and use. Furthermore in another preferred embodiment the rack is reversibly attached to the cuff and is thus, reusable. This is important, if one-way cuffs or cuffs of different sizes are employed in individual measurements.

In another preferred embodiment the rack comprises the coding element. In a preferred variant the rack comprises a coding element encoding information for ensuring the correct use of the components of the system and matching of the system to the individual patient during blood pressure measurements and the rack itself is attached to the cuff. Preferably the coding element encodes at least the correct size of the cuff and/or a number and/or a name that identifies the individual patient for instance in a central database.

The invention further includes a method for the identification of one or more system components of a non-invasive blood pressure system, without the need for placement of the system components to the body of a patient. The method comprises the following steps of:

a) providing a monitor with a reading unit and one or more further system components with a coding element and
b) tagging of the system components by the reading unit of the monitor via read-out of information encoded by the coding element of the system components.

In a preferred embodiment of the method according to the invention the information obtained by reading the coding element is compared with pre-determined information for a specific patient to ensure the correct assembly of the NIBP system for that particular patient. For example, if a cuff size interpreted from the coding element does not agree with pre-determined information for a particular patient, the monitor suggests the correct cuff size to the operator. Preferably, this is displayed in a display associated with the monitor. The pre-determined information is preferably obtained from a server having access to the patient's electronic medical record or it is inputted to the system by the operator or it is encoded directly in a coding element.

In another preferred embodiment the monitor is configured to automatically adjust operational characteristics of the NIBP system based on the read parameters in order to optimize the NIBP readings taken by the assembly of the NIBP system. For example, if the patient is an infant or child, the settings of the monitor can be adjusted accordingly, for instance the correct overpressure safety limit is automatically selected, thereby ensuring patient safety and accuracy of the measurement.

In a further preferred embodiment both the cuff and the hose comprise coding elements. In this example the system checks, prior to application of the system to a patient, whether the different components match each other and will match the patient they will be applied to.

In a yet another preferred embodiment of the inventive method the monitor is held by a rack comprising a coding element and the rack is attached to a cuff. In a preferred variant of such an assembly, data on the correct cuff size for the next patient is available to the system prior to application of the cuff attached to the rack to the patient. Preferably the system determines, which cuff size will be used, through reading the coding element comprised in the rack. If the cuff size matches the particular patient the blood pressure measurement is preferably started automatically. If the cuff size does not match the particular patient the inflation mechanism is blocked, thereby increasing patient safety as well as the accuracy of the measurement. Moreover in such a case the monitor preferably gives instructions to the operator about a different component e.g. cuff that suits the particular patient better, thereby improving user guidance. However, preferably an appropriate override is provided to unlock the mechanism and allow the NIBP measurements to proceed, even if optimal matching of the components was not possible given a particular patient situation.

In another preferred embodiment the method also comprises the step of providing a rack comprising the coding element which is permanently or reversibly attached to a cuff.

In a further preferred embodiment of the inventive method the cuff comprising the rack is applied to a patient. In the next step the monitor is applied to the rack and the hose is applied so that it connects the monitor and the cuff. Subsequently the information encoded by the coding element comprised in the hose and/or the rack is read by the reader comprised in the monitor to identify the individual patient. Then blood pressure is determined. The outcome of the measurement is saved together with the information encoded by coding element so that the blood pressure reading is correctly allocated to the specific patient.

In a further preferred embodiment of the inventive method the tagging of the system components by the reading unit occurs by electromagnetic radiation, even more preferably by high frequency transmission or infrared transmission.

In yet another preferred embodiment the method also comprises the step of providing a coding element which is a radio-frequency identity (RFID) tag or a bar code.

In another preferred embodiment the method also comprises the step of providing a coding element readable by high frequency transmission or infrared transmission.

In a further preferred embodiment the method also comprises the step of providing a writable coding element.

In a preferred embodiment the outcome of the blood pressure measurement is stored together with a unique number or a patient identifier on the writable coding element of at least one system component.

In another preferred embodiment the inventive method further comprises the step of automatic correlation of the outcome of the blood pressure measurement with the patient data by linking of the information encoded by the coding element with the measurement data and the patient record.

As used herein the term "linking" refers to the connection of specific information encoded by the coding element with other relevant data, e.g. by assigning this information to other relevant data such as the results from the blood pressure measurement and the data of the patient record.

In a particular preferred embodiment of this method step a unique number or a patient identifier is read out from the coding element of at least one system component and this unique number or the patient identifier is stored together with the outcome of the blood pressure measurement in the record of the patient. Preferably the record of the patient is saved in a separate device such as a central database.

In a further preferred embodiment of this method step the patient data, e.g. a patient identifier, is written onto the coding element of at least one system component. Thus the outcome of the blood pressure measurement, which is saved together which this patient identifier can subsequently be allocated to the corresponding patient record and stored in that record.

In yet another preferred embodiment of this method the coding element of a least one system component holds a unique number. This number is allocated to a particular patient in a first step. Thus again the outcome of the blood pressure measurement, which is saved together with this specific number can subsequently be allocated to the corresponding patient record and stored in that record.

In preferred embodiment the method further comprises the step of providing at least one further system component selected from the group consisting of a cuff, a rack, an analysis unit, a measuring device, a reading unit, an electronic pressure transducer (pressure sensor), a connecting hose, an extension hose, a microphone, a battery pack, a display and a deflating/inflating mechanism (air pump).

Even though the described embodiments are explained in reference to NIBP monitoring systems and methods, the inventive system and method may be readily applied to different fields as well, such as other medical sensors, patient monitors, defibrillators and home healthcare products

DESCRIPTION OF PREFERRED EMBODIMENTS

The following figures illustrate schematically the essential aspects of the invention.

It is to be understood that the figures are by no means meant as to limit the scope of the invention.

Figure 1:
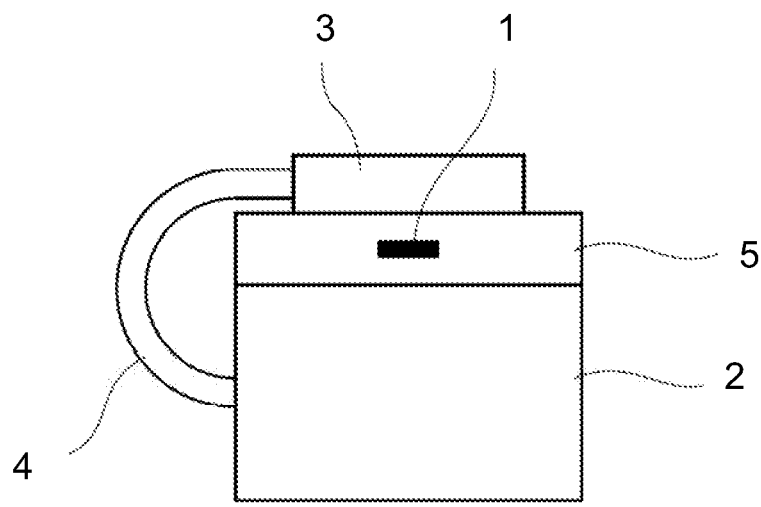
FIG. 1 shows, in an exemplary fashion, a preferred embodiment of a NIBP system according to the invention, characterized in that the rack 5 comprises a coding element 1.

FIG. 1 shows a cuff 2 comprising a rack 5, wherein the rack 5 comprises a coding element 1. The rack 5 is designed to hold the monitor 3, which is connected to the cuff 2 only via a hose 4 for inflating and deflating the cuff 4. The hose 4 may be permanently attached to either the monitor 3 or the cuff 4 or may be disconnectable from both.

Thus the information encoded by the coding element 1 comprised in the rack 5 can be used to identify the particular cuff and/or the patient and/or can be used to allocate the blood pressure measurement outcome to the specific patient.

Figure 2:
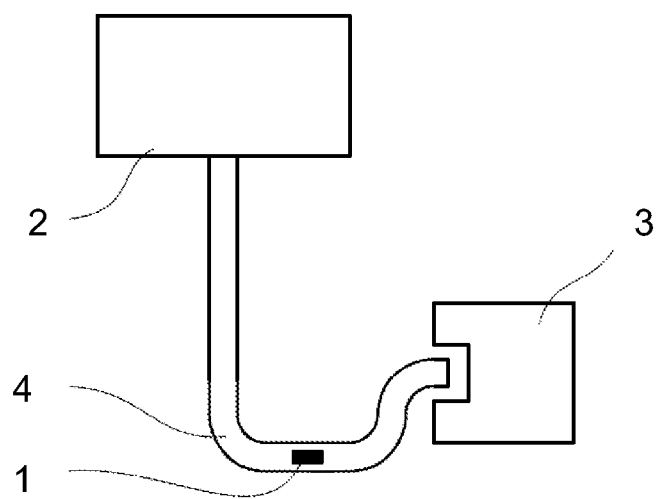
FIG. 2 shows, in an exemplary fashion, a preferred embodiment of a NIBP system according to the invention, characterized in that the hose 4 comprises a coding element 1 and is disconnectable from the monitor 3.

FIG. 2 shows a hose 4, which comprises a coding element 1. The hose 4 is permanently connected to a cuff 2 and can be reversibly attached to a monitor 3. Thus the information encoded by the coding element 1 comprised in the hose 4 can be used to identify the particular cuff 2.

Not shown is the preferred embodiment, in which both the cuff 2 and the hose 4 comprise a coding element 1 so that the monitor 3 unambiguously indentifies both of these specific components and compares the obtained information with pre-determined information for a specific patient. In a preferred variant of this setting blood pressure measurement ideally would only be initialized when the obtained information matches the pre-determined information.

Figure 3:
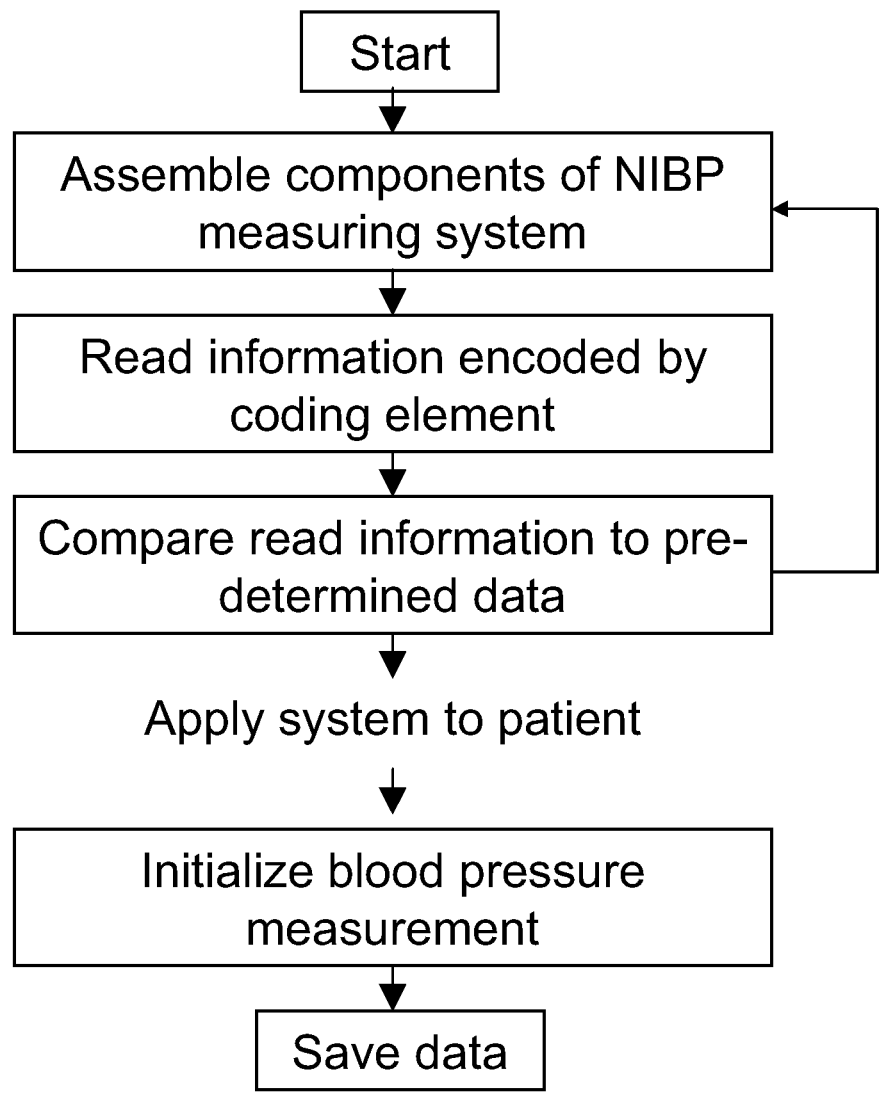
FIG. 3 shows, in an exemplary fashion a preferred embodiment of a method according to the invention, characterized in that system automatically compares the information read from the coding element 1 with pre-determined information.

FIG. 3 shows a flowchart of the method, in which the system automatically compares the information read from the coding element 1 with pre-determined information. In the first step the components of the NIBP system for instance the cuff 2, the rack 5, the hose 4 and the monitor 3 are assembled. Then the information encoded by the coding element(s) 1 is read and subsequently the monitor 3 checks whether the different components are compatible or the obtained information is compared to predetermined information. For example the cuff size a specific patient requires is already known. In that case the monitor 3 can verify that the used cuff size matches the pre-determined cuff size. If the pre-determined data does not match the obtained data the system provides guidance to the operator for instance on which cuff size is the correct one for the specific patient. If the two sets of data match blood pressure measurement is initialized, preferably automatically. Or if the information encoded by the coding element was read prior to application of the system to a patient, the system has to be applied before the measurement can be initialized.

Figure 4:
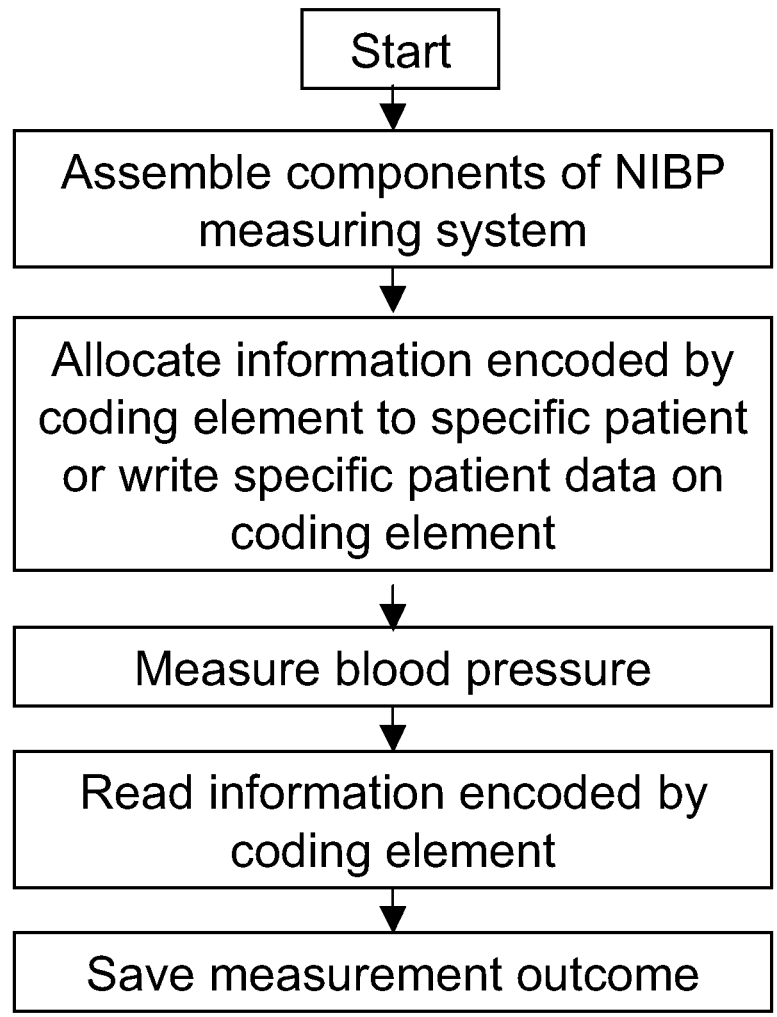
FIG. 4 shows, in an exemplary fashion a preferred embodiment of a method according to the invention, characterized in that the system automatically saves the outcome of the NIBP measurement together with a patient identifier.

FIG. 4 shows a flowchart of the method, in which the system automatically saves the outcome of the NIBP measurement to the record of a patient. The system allocates the outcome of the measurement to the record of the patient through reading out a unique number or patient ID encoded by the coding element. For example in the first step the components of the NIBP system for instance the cuff 2, the rack 5, the hose 4 and the monitor 3 are assembled and the information encoded by a coding element 1 of at least one system component is allocated to the specific patient or specific patient data is written on coding element 1. Then the system is applied to the patient and blood pressure is determined. In the next step the information encoded by the coding element 1 is read to obtain patient specific information. For instance a unique identity number encoded by the coding element 1 was allocated to a specific patient and is now read from the coding element. This encoded information is used in the last step to save the outcome of the measurement to the record of the specific patient.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

LIST OF REFERENCE NUMBERS

1 Coding element
2 Cuff
3 Monitor
4 Hose
5 Rack

The invention claimed is:

1. A method for the identification of a plurality of system components of a non-invasive blood pressure system, the method comprising:
   wirelessly identifying a plurality of system components that include unique coding elements that encode information with a reading unit of a monitor including reading-out the information encoded by the coding element of the system components without attaching the identified system components to a body of a patient;
   wherein the plurality of identified system components includes a hose and at least one of a cuff and a rack; and
   checking, with the monitor, a compatibility of the identified hose component with each other identified system component based on the information encoded by the respective coding elements.

2. The method according to claim 1, wherein the wireless identification of the system components is read by the reading unit via at least one of electromagnetic radiation, high frequency transmission and infrared transmission.

3. The method according to claim 1, further including:
   reading a patient identifier from the coding elements of the system components;
   automatically correlating an outcome of a blood pressure measurement with patient data by linking of the information encoded by the coding element with outcome of a blood pressure measurement and a patient record.

4. The method according to claim 1, further including:
reading a patient identification from the coding elements of the system components;
determining if the system components are a correct assembly for the patient identification;
automatically starting a blood pressure measurement in response to the system components being in a correct assembly for the patient identification; and
suggesting a correct assembly for the patient identification in response to the system components being in an incorrect assembly for the patient identification.

5. A non-invasive blood pressure measuring system, the system comprising:
a monitor;
a plurality of further system components including a hose and at least one of a cuff and a rack, each of the plurality of further system components including a coding element encoding information; and
a reading unit configured to wirelessly identify at least two of the further system components by reading the information encoded by the coding element of each of the further system components;
wherein the monitor is configured to check a compatibility of the identified hose component with each other identified further system component based on the information encoded by the respective coding elements.

6. The non-invasive blood pressure system according to claim 5, wherein each coding element is configured to be read by the reading unit without attaching the further system components to a body of a patient.

7. The non-invasive blood pressure system according to claim 5, wherein each coding element encodes information that is readable using the monitor via at least one of electromagnetic radiation, high frequency transmission, or infrared transmission.

8. The non-invasive blood pressure system according to claim 5, wherein at least one coding element includes a patient identification.

9. The non-invasive blood pressure system according to claim 8, wherein the monitor is configured to automatically correlate an outcome of a blood pressure measurement with the patient identification by linking the information encoded by the coding element with measurement data and storing the measurement data in a patient record of the identified patient.

10. The non-invasive blood pressure system according to claim 8, wherein the monitor is configured to automatically adjust operational characteristics of the system based on the identified further system components and the patient identification.

11. The non-invasive blood pressure system according to claim 8, wherein the monitor is configured to compare the identified further system components with assembly information corresponding to the patient identification to ensure a correct assembly of the further system components for the identified patient.

12. The non-invasive blood pressure system according to claim 11, wherein in response to an incorrect assembly of the system being used for the patient identification, the monitor is configured to suggest a correct assembly.

13. A non-invasive blood pressure monitoring system comprising:
a pressure cuff configured to be fitted over a limb of a patient;
a cuff coding element attached to the pressure cuff and configured to store encoded information including at least an identification of characteristics of the pressure cuff;
a hose configured to be attached to the pressure cuff;
a hose coding element attached to the hose and configured to store encoding information including at least an identification of characteristics of the hose; and,
a monitor configured to be attached to the hose and being configured to:
read the cuff coding element and the hose coding element, and
determine the compatibility of the pressure cuff and hose.

14. The non-invasive blood pressure monitoring system according to claim 13, wherein at least one of the coding elements is configured to store patient specific data and the monitor is further configured to:
access patient electronic files based on the stored patient specific data,
determine if the pressure cuff and hose are compatible with the patient.

15. The non-invasive blood pressure measuring system according to claim 14, wherein the monitor is configured to automatically correlate an outcome of a blood pressure measurement with the patient by linking with the patient electronic files.

16. The non-invasive blood pressure system according to claim 14, wherein, in response to the pressure cuff and hose being determined to be compatible with the identified patient, the monitor is further configured to automatically compute and adjust a blood pressure measurement based on the identified pressure cuff and hose with linked information encoded by the coding elements.

17. The non-invasive blood pressure monitoring system according to claim 13, further including:
a rack configured to be connected with the pressure cuff;
a rack coding element attached to the rack and configured to store encoded information including at least one of an identification of characteristics of the cuff or a patient identifier.

18. The non-invasive blood pressure measuring system according to claim 13, wherein each of the coding elements encodes information that is readable at the monitor by receipt of at least one of electromagnetic radiation, high frequency transmission, and infrared transmission.

19. The non-invasive blood pressure measuring system according to claim 13, wherein each of the coding elements is a radiofrequency identity (RFID) tag or a bar code.

* * * * *